US008897892B2

(12) United States Patent
Fuhs et al.

(10) Patent No.: US 8,897,892 B2
(45) Date of Patent: Nov. 25, 2014

(54) SUTURE SLEEVES HAVING EXTERIOR SURFACE TEAR RESISTANCE (71) Applicant: Cardiac Pacemakers, Inc., St. Paul, MN (US)

(72) Inventors: Christopher A. Fuhs, Roseville, MN (US); Patrick S. McManaman, Maple Grove, MN (US); Kimberly A. Morris, Minneapolis, MN (US); Yevgenia Sheikholeslami, Minneapolis, MN (US); Brendan E. Koop, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/064,655

(22) Filed: Oct. 28, 2013

(65) Prior Publication Data
US 2014/0121739 A1    May 1, 2014

Related U.S. Application Data (60) Provisional application No. 61/719,752, filed on Oct. 29, 2012.

(51) Int. Cl.
*A61N 1/00* (2006.01)
*A61N 1/05* (2006.01)

(52) U.S. Cl.
CPC *A61N 1/05* (2013.01); *A61N 1/056* (2013.01); *A61N 2001/0582* (2013.01)
USPC .......................................................... 607/116

(58) Field of Classification Search
CPC .. A61N 1/05; A61N 1/056; A61N 2001/0582
USPC .......................................................... 607/116
See application file for complete search history.

(56) References Cited

U.S. PATENT DOCUMENTS 4,266,552 A    5/1981   Dutcher et al.
4,276,882 A    7/1981   Dickhudt et al.
(Continued)

FOREIGN PATENT DOCUMENTS

EP    1314449 A2    5/2003
EP    2275169 A1    1/2011
(Continued)

OTHER PUBLICATIONS

Pacing Lead Stabilizer with Modified Slit Geometry, Technical Disclosure from www.ip.com, No. IPCOM000130753D, published Nov. 3, 2005, full document available at http://www.ip.com/pubview/IPCOM000125732D,6 pages.

(Continued)

*Primary Examiner* — George Manuel
(74) *Attorney, Agent, or Firm* — Faegre Baker Daniels LLP (57) ABSTRACT Various embodiments concern a suture sleeve for securing an implantable lead with a suture. The suture sleeve can comprise a tubular body having a proximal end portion, a distal end portion, an exterior surface, and a lumen, the lumen sized to receive the implantable lead. The suture sleeve can further comprise a suture receiving area along the tubular body, the suture receiving area within a channel that extends around a circumference of the tubular body. An exterior surface of the suture receiving area can comprise a tear resistant feature. The tear resistant feature can be configured to resist initiation of a tear in the exterior surface from the suture. The lumen can comprise an inner surface configured to frictionally engage the implantable lead.

20 Claims, 3 Drawing Sheets (56) References Cited

U.S. PATENT DOCUMENTS

| | | | |
|---|---|---|---|
| 4,287,891 A | 9/1981 | Peters |
| 4,301,815 A | 11/1981 | Doring |
| 4,387,727 A | 6/1983 | Sandstrom |
| 4,409,994 A | 10/1983 | Doring |
| 4,437,475 A | 3/1984 | White |
| 4,442,840 A | 4/1984 | Wojciechowicz, Jr. |
| 4,516,584 A | 5/1985 | Garcia |
| 4,519,404 A | 5/1985 | Fleischhacker |
| 4,538,623 A | 9/1985 | Proctor et al. |
| 4,550,737 A | 11/1985 | Osypka |
| 4,553,961 A | 11/1985 | Pohndorf et al. |
| 4,585,013 A | 4/1986 | Harris |
| 4,613,329 A | 9/1986 | Bodicky |
| 4,615,472 A | 10/1986 | Nash |
| 4,672,979 A | 6/1987 | Pohndorf |
| 4,676,782 A | 6/1987 | Yamamoto et al. |
| 4,683,895 A | 8/1987 | Pohndorf |
| 4,768,523 A | 9/1988 | Cahalan et al. |
| 4,796,643 A | 1/1989 | Nakazawa et al. |
| 4,906,233 A | 3/1990 | Moriuchi et al. |
| 5,036,862 A | 8/1991 | Pohndorf |
| 5,107,856 A | 4/1992 | Kristiansen et al. |
| 5,129,405 A | 7/1992 | Milijasevic et al. |
| 5,152,298 A | 10/1992 | Kreyenhagen et al. |
| 5,242,431 A | 9/1993 | Kristiansen |
| 5,257,975 A | 11/1993 | Foshee |
| 5,273,053 A | 12/1993 | Pohndorf |
| 5,366,496 A | 11/1994 | Dahl et al. |
| 5,376,108 A | 12/1994 | Collins et al. |
| 5,423,763 A | 6/1995 | Helland et al. |
| 5,476,493 A | 12/1995 | Muff |
| 5,484,445 A | 1/1996 | Knuth |
| 5,549,619 A | 8/1996 | Peters et al. |
| 5,583,319 A | 12/1996 | Lieurance |
| 5,584,874 A | 12/1996 | Rugland et al. |
| 5,603,730 A | 2/1997 | Romkee |
| 5,628,780 A | 5/1997 | Helland et al. |
| 5,674,273 A | 10/1997 | Helland |
| 5,683,403 A | 11/1997 | Adams et al. |
| 5,683,446 A | 11/1997 | Gates |
| 5,709,644 A | 1/1998 | Bush |
| 5,735,891 A | 4/1998 | White |
| 5,746,722 A | 5/1998 | Pohndorf et al. |
| 5,824,032 A | 10/1998 | Belden |
| 5,827,296 A | 10/1998 | Morris et al. |
| 5,843,146 A | 12/1998 | Cross, Jr. |
| 5,871,528 A | 2/1999 | Camps et al. |
| 5,876,429 A | 3/1999 | Schroeppel |
| 5,957,968 A | 9/1999 | Belden et al. |
| 6,002,969 A | 12/1999 | Machek et al. |
| 6,134,477 A | 10/2000 | Knuteson |
| 6,173,206 B1 | 1/2001 | Shchervinsky |
| 6,259,953 B1 | 7/2001 | Lucchesi et al. |
| 6,463,334 B1 | 10/2002 | Flynn et al. |
| 6,473,654 B1 | 10/2002 | Chinn |
| 6,554,802 B1 | 4/2003 | Pearson et al. |
| 6,592,553 B2 | 7/2003 | Zhang et al. |
| 6,643,550 B2 | 11/2003 | Westlund et al. |
| 6,895,277 B2 | 5/2005 | Westlund et al. |
| 6,901,287 B2 | 5/2005 | Davis et al. |
| 6,912,423 B2 | 6/2005 | Ley et al. |
| 6,915,169 B2 | 7/2005 | Flynn et al. |
| 6,921,295 B2 | 7/2005 | Sommer et al. |
| 6,985,777 B2 | 1/2006 | Tsuboi et al. |
| 7,082,337 B2 | 7/2006 | Sommer et al. |
| 7,090,660 B2 | 8/2006 | Robert et al. |
| 7,184,841 B1 | 2/2007 | Bodner et al. |
| 7,218,972 B2 | 5/2007 | Rodriguez |
| 7,242,986 B2 | 7/2007 | Rodriguez |
| 7,248,930 B1 | 7/2007 | Woloszko et al. |
| 7,398,125 B2 | 7/2008 | Osypka et al. |
| 7,747,334 B2 | 6/2010 | Bly et al. |
| 7,765,015 B2 | 7/2010 | Johnson et al. |
| 7,806,886 B2 | 10/2010 | Kanderian, Jr. et al. |
| 7,914,582 B2 * | 3/2011 | Felt et al. .................. 623/20.16 |
| 8,000,811 B2 | 8/2011 | Hill |
| 2003/0050668 A1 | 3/2003 | Lee |
| 2003/0130616 A1 | 7/2003 | Steil et al. |
| 2003/0195600 A1 | 10/2003 | Tronnes et al. |
| 2003/0220678 A1 | 11/2003 | Tronnes et al. |
| 2004/0059403 A1 | 3/2004 | Massullo |
| 2004/0093052 A1 | 5/2004 | Westlund et al. |
| 2004/0143216 A1 | 7/2004 | Douglas et al. |
| 2004/0254623 A1 | 12/2004 | Rodriguez et al. |
| 2005/0080470 A1 | 4/2005 | Westlund et al. |
| 2005/0137664 A1 | 6/2005 | Sommer et al. |
| 2005/0177220 A1 | 8/2005 | Iaizzo et al. |
| 2005/0202703 A1 | 9/2005 | Westlund et al. |
| 2005/0267557 A1 | 12/2005 | Flynn et al. |
| 2006/0235484 A1 | 10/2006 | Jaax et al. |
| 2006/0264803 A1 | 11/2006 | Lui et al. |
| 2007/0078399 A1 | 4/2007 | Olson |
| 2007/0156216 A1 | 7/2007 | McAuliffe et al. |
| 2007/0225784 A1 | 9/2007 | Bly et al. |
| 2007/0282412 A1 | 12/2007 | Soltis et al. |
| 2007/0282414 A1 | 12/2007 | Soltis et al. |
| 2007/0282415 A1 | 12/2007 | Tockman et al. |
| 2007/0293922 A1 | 12/2007 | Soltis et al. |
| 2008/0228251 A1 | 9/2008 | Hill |
| 2008/0262587 A1 | 10/2008 | Flynn et al. |
| 2008/0262588 A1 | 10/2008 | Zarembo et al. |
| 2009/0125058 A1 | 5/2009 | Bodner et al. |
| 2009/0125059 A1 | 5/2009 | Verzal et al. |
| 2009/0125060 A1 * | 5/2009 | Rivard et al. .................. 606/232 |
| 2009/0125061 A1 | 5/2009 | Rivard et al. |
| 2009/0326473 A1 | 12/2009 | Rosenberg et al. |
| 2010/0016801 A1 | 1/2010 | Rosenberg et al. |
| 2010/0114034 A1 | 5/2010 | Wright et al. |
| 2011/0009935 A1 | 1/2011 | Kane et al. |
| 2012/0029335 A1 | 2/2012 | Sudam et al. |
| 2012/0071959 A1 | 3/2012 | Helgesson |
| 2012/0330354 A1 | 12/2012 | Kane et al. |
| 2013/0138200 A1 | 5/2013 | Mayberry et al. |
| 2013/0158640 A1 | 6/2013 | Soltis et al. |
| 2014/0128948 A1 | 5/2014 | Clark et al. |

FOREIGN PATENT DOCUMENTS

WO  WO2006116454 A2  11/2006
WO  WO2007024164 A1  1/2007

OTHER PUBLICATIONS

Suture Sleeve with Removable Fins, Technical Disclosure from www.ip.com, No. IPCOM000125732D, published Jun. 15, 2005, full document available at http://www.ip.comlpubviewIIPCOM000125732D, 4 pages.

International Search Report and Written Opinion issued in PCT/US2013/067138, mailed Mar. 20, 2014, 13 pages.

* cited by examiner

SUTURE SLEEVES HAVING EXTERIOR SURFACE TEAR RESISTANCE

CROSS-REFERENCE TO RELATED APPLICATION

This application claims priority to Provisional Application No. 61/719,752, filed Oct. 29, 2012, which is herein incorporated by reference in its entirety.

TECHNICAL FIELD

The present disclosure relates generally to implantable medical leads. More specifically, the disclosure relates to a suture sleeve for an implantable medical lead assembly.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of a pulse generator (PG) such as a pacemaker, an implantable cardioverter defibrillator (ICD), or a cardiac resynchronization (CRT) device. Such devices are typically coupled to one or more implantable leads having one or more electrodes that can be used to deliver pacing therapy and/or electrical shocks to the heart. Implantable leads can additionally or alternatively be used to stimulate other nervous and/or musculature systems of the body. Whether for a cardiac lead or for a lead used elsewhere in the body, a suture sleeve can be provided along the lead to anchor the lead.

SUMMARY

Example 1 concerns a suture sleeve for securing an implantable lead with a suture, the suture sleeve comprising: a tubular body having a proximal end portion, a distal end portion, and an exterior surface; a lumen within the tubular body extending from the proximal end portion to the distal end portion, the lumen sized to receive the implantable lead; a suture receiving area along the tubular body, the suture receiving area defining an exterior surface within a channel that extends around a circumference of the tubular body; a tear resistant feature extending along at least part of the suture receiving area, the tear resistant feature configured to resist initiation of a tear in the exterior surface from the suture; and an inner surface within the lumen, the inner surface configured to frictionally engage the implantable lead.

In example 2, the suture sleeve of example 1, wherein the tear resistant feature comprises texturing along the suture receiving area.

In example 3, the suture sleeve of either of example 1 or 2, wherein the texturing reduces the surface area of the exterior surface of the suture receiving area in contact with the suture when the suture is placed along the suture receiving area.

In example 4, the suture sleeve of example 2, wherein the texturing comprises a pattern of crossing raised lines.

In example 5, the suture sleeve of example 2, wherein the texturing comprises a plurality of dimples.

In example 6, the suture sleeve of any of examples 1-5, wherein the texturing comprises a pattern of grooves.

In example 7, the suture sleeve of any of examples 1-6, wherein the tear resistant feature reduces friction between the exterior surface and the suture when the suture is placed within the channel of the suture receiving area.

In example 8, the suture sleeve of any of examples 1-7, wherein the tear resistant feature comprises a hardened material defining the exterior surface of the suture receiving area and the exterior surface of the suture receiving area is harder relative to the inner surface within the lumen.

In example 9, the suture sleeve of any of examples 1-8, wherein the exterior surface of the suture receiving area is formed from a first material and the inner surface of the lumen is formed from a second material, the first material having a higher durometer than the second material.

In example 10, the suture sleeve of any of examples 1-9, wherein the suture sleeve is made from a single type of material processed along the suture receiving area to form the tear resistant feature.

In example 11, the suture sleeve of any of examples 1-10, wherein the tear resistant feature comprises a lubricious coating.

In example 12, the suture sleeve of any of examples 1-11, wherein the suture receiving area is between the proximal end portion and the distal end portion; and the channel of the suture receiving area is dimensioned such that a section of suture does not extend above either of the proximal end portion and the distal end portion when the section of the suture is within the channel and contacts the exterior surface of the suture receiving area.

In example 13, the suture sleeve of any of examples 1-12, wherein the tear resistant feature extends only along the suture receiving area.

In example 14, the suture sleeve of any of examples 1-13, wherein the tear resistant feature extends from the proximal end portion to the distal end portion.

Example 15 concerns a suture sleeve for securing an implantable lead with a suture, the suture sleeve comprising a tubular body having a proximal end and a distal end; a lumen within the tubular body extending from the proximal end to the distal end, the lumen sized to receive the implantable lead; an exterior surface extending from the proximal end to the distal end of the tubular body, the exterior surface including a suture receiving area; an inner surface within the lumen, the inner surface configured to frictionally engage the implantable lead; a first material forming at least the suture receiving area of the exterior surface; and a second material forming the inner surface of the lumen, wherein the first material has a higher durometer than the second material and the first material is resistant to initiation of a tear in the exterior surface from the suture.

In example 16, the suture sleeve of example 15, wherein the first material is extruded over the second material to form the tubular body.

In example 17, the suture sleeve of either of examples 15 or 16, wherein the second material is silicone and the first material comprises one or both of a polymer material and a metal material.

Example 18 concerns a method of making a suture sleeve for use with a suture for securing an implantable lead, the method comprising forming a tubular body having a proximal end portion, a distal end portion, an exterior surface, a lumen sized to receive the implantable lead, an inner surface within the lumen, and a channel around the circumference of the tubular body, the channel sized to accommodate the suture within the channel; and processing the exterior surface at least along the channel, the processing providing a tear resistance property of the exterior surface, wherein the processing step is not performed for the inner surface.

In example 19, the method of example 18, wherein processing the exterior surface along the channel comprises hardening a material that forms the exterior surface.

In example 20, the method of either of examples 18 or 19, wherein processing the exterior surface along the channel comprises forming a textured pattern in the exterior surface.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the subject matter of the present disclosure is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1A:
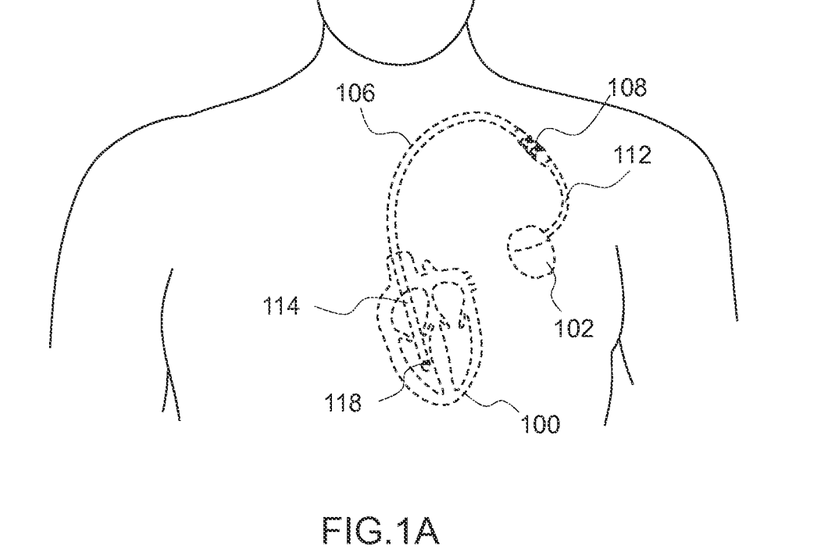
FIG. 1A is a schematic illustration of an implantable medical system including a suture sleeve.

FIG. 1A is a schematic illustration of a pulse generator 102 implanted within a patient. The embodiment of FIG. 1A shows the pulse generator 102 arranged for delivering electrical stimulation to the heart 100. The pulse generator 102 is typically implanted subcutaneously within an implantation location or pocket in the patient's chest or abdomen. The pulse generator 102 is connected to an implantable lead 106. The lead 106 operates to convey electrical signals between the implantable pulse generator 102 and the heart 100. The lead 106 includes a flexible lead body having a proximal end portion 112 and a distal end portion 114. In various embodiments, the lead 106 enters the vascular system through a vascular entry site formed in the wall of the left subclavian vein. Other suitable vascular access sites may be utilized in various other embodiments. The lead 106 can extend through the left brachiocephalic vein and the superior vena cava such that one or more electrodes 118 disposed on the distal end portion 114 of the lead 106 can be implanted in the right atrium, right ventricle, left ventricle, or other location.

The proximal end portion 112 of the lead 106 can extend subcutaneously or submuscularly from the pulse generator 102 to the vascular entry site. Any excess lead length, i.e., length beyond that needed to reach from the pulse generator 102 location to the desired intracardiac implantation site, can be coiled up in the subcutaneous pocket near the pulse generator 102. At least a portion of the lead 106 can be secured by suturing the lead 106 to subcutaneous tissue. The lead 106 can be secured by one or more sutures extending around the body of the lead 106 at a location proximal to the vascular entry site. In particular, the one or more sutures can wrap around a suture sleeve 108 that extends around the body of the lead 106, as will be discussed further herein. Although the pulse generator 102, the lead 106, and the suture sleeve 108 are illustrated in an arrangement for providing therapy to the heart 100, such components can be provided for sensing and/or stimulating various other organs, areas, nerves, or musculature of the body.

Figure 1B:
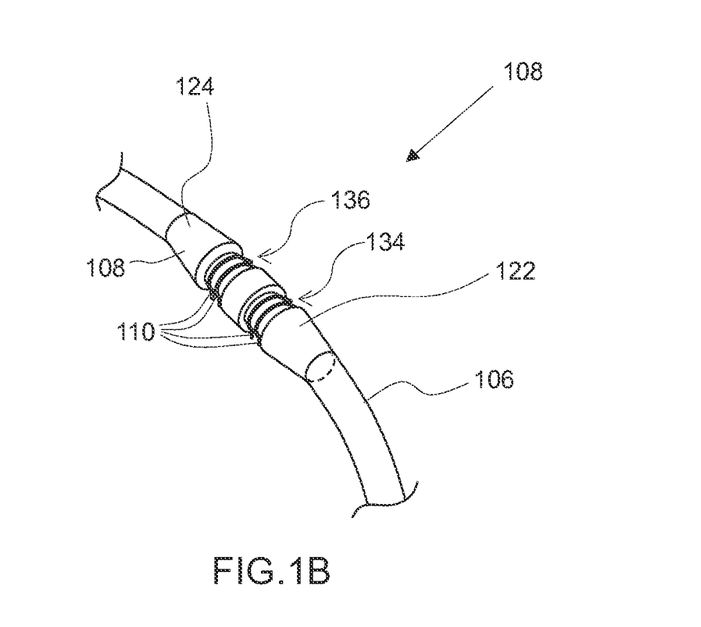
FIG. 1B is an enlarged schematic illustration of the suture sleeve of FIG. 1A sutured at the implant site.

FIG. 1B is an enlarged schematic illustration of the suture sleeve 108 of FIG. 1A. As shown in FIG. 1B, the lead 106 extends through the suture sleeve 108. A plurality of sutures 110 extend around the suture sleeve 108 and engage tissue (not shown). Each suture 110 can comprise a flexible string that can be wrapped around the suture sleeve 108 and threaded through tissue at an implant site. A knot can be tied in each suture 110 after the suture 110 is firmly wrapped around the suture sleeve 108 and thread through tissue at an implant site to anchor the suture sleeve 108 and the lead 106 to the implant site. Frictional engagement between an inner lumen surface of the suture sleeve 108 and an exterior surface of the lead 106 can affix the lead 106 to the suture sleeve 108. The suture sleeve 108 can prevent the sutures 110 from contacting the lead 106 to prevent the sutures 110 from damaging the lead 106 while also securing the lead 106 at an implant site.

The suture sleeve 108 can comprise a tubular body having a proximal end portion 122 and a distal end portion 124. The suture sleeve 108 can further comprise a proximal suture receiving area 134 and a distal suture receiving area 136 between the proximal end portion 122 and the distal end portion 124. Each of the proximal and distal suture receiving areas 136 and 134 can comprise a channel that extends around the circumference of the suture sleeve 108. Reception of the sutures 110 within the channels can prevent the sutures 110 from slipping off of the suture sleeve 108. Although shown having two suture receiving areas, additional embodiments can include one or more than two suture receiving areas.

Figure 2A:
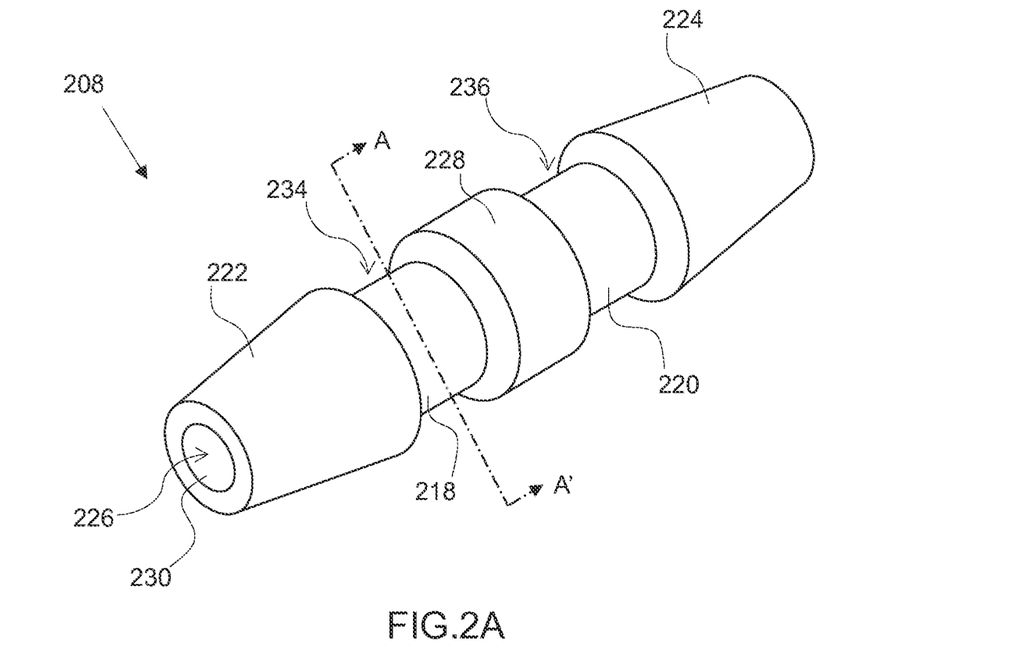
FIG. 2A is a perspective view of a suture sleeve having a tear-resistant outer radial region.

FIG. 2A is a perspective view of a suture sleeve 208. The suture sleeve 208 of FIG. 2A can correspond with the suture sleeve 108 of FIGS. 1A and 1B. The suture sleeve 208 can include a proximal end portion 222, a middle portion 228, a distal end portion 224, and a lumen 226 that extends from the proximal end portion 222 to the distal end portion 224. The lumen 226 is defined by an inner surface 230 of the suture sleeve 208. The lumen 226 can be dimensioned such that the inner surface 230 can press against and grip (e.g., via friction) the outer surface of the lead 106. For example, the diameter of the lumen 226 may be slightly smaller than the outer diameter of the lead 106, and the lumen 226 can be elastically expandable to allow the suture sleeve 208 to be placed over the lead 106. In some embodiments, the diameter of the lumen 226 is about the same as the outer diameter of the lead 106. In some embodiments, the diameter of the lumen 226 may be slightly larger than the outer diameter of the lead 106. In various embodiments, the suture sleeve 208 can slide along the lead 106 until a suture 100 is wrapped around the suture sleeve 208 to press the inner surface 230 against the lead 106.

Each of the proximal suture receiving area 234 and the distal suture receiving area 236 can comprise, or be defined by, a channel that extends circumferentially around the suture sleeve 208. In the case of the proximal suture receiving area 234, the channel can be defined by an exterior surface section 218, where the walls of the channel consist of the proximal end portion 222 and the middle portion 228, the proximal end portion 222 and the middle portion 228 each having an outer diameter greater than the outer diameter of the exterior surface of the proximal suture receiving area 234. In the case of the distal suture receiving area 236, the channel can be defined by an exterior surface section 220, where the walls of the channel consist of the distal end portion 224 and the middle portion 228, the distal end portion 224 and the middle portion 228 each having an outer diameter greater than the outer diameter of the exterior surface of the distal suture receiving area 236. Each of the channels can be dimensioned for receiving a suture entirely within the channel such that a section of a suture does not extend above the outer diameter of the proximal end portion 222, the middle portion 228, and/or the distal end portion 224 when the section of the suture is contacting proximal or distal suture receiving areas 234 and 236.

Various aspects of the present disclosure concern features for preventing the initiation of tears along the exterior surfaces of suture sleeves. Tears in a suture sleeve can occur for various reasons. In some cases, an overly tightened suture can apply more pressure to a suture sleeve than intended. Suture sleeves could be torn from stress that results from frictional interaction with the sutures. In some cases, a suture sleeve can be torn by opposing frictional forces developed by the relative movement of multiple strands of a suture in opposite directions during suture tie-down. As such, a suture can create a small tear in the outer surface of a suture sleeve. Because a small tear from a suture can propagate within the suture sleeve, stopping the creation of a small tear on the outer surface of a suture sleeve can be of particular importance. To inhibit the initiation of a tear on the outer surface of a suture sleeve, one or more tear resistant features can be provided along the exterior surfaces 218 and 220 of the proximal suture receiving area 234 and a distal suture receiving area 236, as further described herein.

The proximal suture receiving area 234 can include a tear resistant feature along the proximal exterior surface 218 and the distal suture receiving area 236 can include a tear resistant feature along the distal exterior surface 220. The tear resistant features along the proximal and distal exterior surfaces 218 and 220 can make the suture sleeve 208 resistant to the initiation of a tear along the outer surfaces of the proximal suture receiving area 234 and the distal suture receiving area 236.

Providing tear resistant features along the proximal and distal suture receiving areas 234 and 236 of the suture sleeve 208 can resist the initiation of a tear at the location where a suture may be most likely to initiate a tear while allowing the remainder of the suture sleeve 208 to be optimized for other functions. For example, the suture sleeve 208 can be made from a soft and elastic silicone material which can allow the suture sleeve 208 to bend with the lead 106 (e.g., providing strain relief along the proximal end portion 222 and the distal end portion 224) while the inner surface 230 of the lumen 226 can grip the lead 106. In some embodiments, the material of the suture sleeve 208 defining the proximal suture receiving area 234 and the distal suture receiving area 236 can be different from the material forming other areas of the suture sleeve 206. For example the proximal end portion 222, the middle portion 228, the distal end portion 224, and the inner surface 230 of the lumen 226 can be formed from silicone while the exterior surfaces defining the proximal suture receiving area 234 and the distal suture receiving area 236 can be formed from a different material or can be treated to modify the silicone (for example, through texturizing and/or hardening).

Figure 2B:
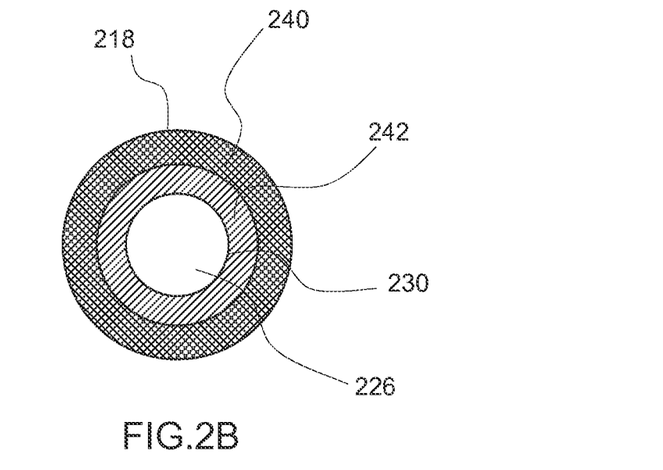
FIG. 2B is a cross-sectional view of the suture sleeve of FIG. 2A taken along an axis A-A.

FIG. 2B is a cross-sectional view of the suture sleeve 208 of FIG. 2A taken along an axis A-A. As depicted in FIG. 2B, the suture sleeve 208 along the proximal suture receiving area 234 can be formed from multiple materials. While the cross section of the proximal suture receiving area 234 is shown in FIG. 2B and described below, the suture sleeve 208 can be configured similarly along the distal suture receiving area 236 or other suture receiving area. As shown, the suture sleeve 208 can include a first material 240, the first material defining the proximal exterior surface 218 of the suture sleeve 208 along the proximal suture receiving area 234. The suture sleeve 208 can also include a second material 242 defining the inner surface 230 of the lumen 226 of the suture sleeve 208. In some embodiments, the first material 240 and the second material 242 can be different materials. In some cases, the first material 240 and the second material 242 can be different polymers. For example, the first material 240 can be polyether ether ketone (PEEK), urethane, polyether block amide (PEBA), or polytetrafluoroethylene (PTFE) and the second material can be silicone. In some embodiments, the first material 240 can be a metal and the second material 242 can be a polymer. In some cases, the first material 240 and the second material 242 can be the same polymer, but the first material 240 and the second material 242 can be processed in different ways. For example, the second material 242 can be a soft silicone while the first material 240 can be hardened silicone.

The first material 240 and the second material 242 can have different properties. In some cases, the first material 240 can have a higher durometer than the second material 242. By providing a first material with a higher durometer, the proximal exterior surface 218 of the proximal suture receiving area 234 can resist initiation of a tear. In addition, material having a higher durometer can experience a lesser degree of deformation around a tightening suture, thereby reducing an overall proportion of suture material in contact with the proximal exterior surface 218 of the proximal suture receiving area 234. Reducing contact between the proximal exterior surface 218 and the suture can decrease the opportunities for surface material to be damaged by the suture and can decrease friction along the proximal exterior surface 218. The second material 242 having a lower durometer defining the inner surface 230 of the lumen 226 can accommodate the lead 106 within the lumen 226 (e.g., by expanding), to grip the exterior of the lead 106 (e.g., by conforming to the shape the exterior of the lead 106).

In some embodiments, only a portion of the suture sleeve 208 is made from the first material 240. For example, the first material 240 may be provided only along the proximal and distal exterior surfaces 218 and 220 (e.g., only within the channels of the proximal suture receiving area 234 and the distal suture receiving area 236), the first material 240 being absent along the proximal end portion 222, the middle portion 228, and the distal end portion 224. In some embodiments, the proximal end portion 222, the middle portion 228, and/or the distal end portion 224 can be formed solely from the second material 242. In some embodiments, the entire outer surface of the suture sleeve 208 is defined by the first material 240. While FIG. 2B shows the first material 240 extending entirely around the circumference of the suture sleeve 208, the first material 240 may extend only around a portion of the circumference of the suture sleeve 208 (e.g., less than 180 degree) in some other embodiments.

The first material 240 can be disposed around the second material 242 in various ways. In some cases, the suture sleeve 208 can be co-extruded with the first material 240 being disposed over the second material 242. In some cases, the suture sleeve 208 can be made from an injection molding process. Such an injection molding process may mold the first material 240 over the second material 242. In some cases, the first material 240 can be formed into a tubular structure or other shape that is separate from the second material 242. The tubular structure or other shape can then be elastically stretched over the suture sleeve 208 and placed within a channel of the suture sleeve 208. In some cases, the first material 240 forming the tubular structure or other shape can be exposed to heptane or other chemicals prior to being placed within a channel of the suture sleeve 208. The heptane or other chemical can allow the first material 240 to expand. The tubular structure or other shape can then contract and tighten around the suture sleeve 208 within the channel as the heptane or other chemical evaporates.

In some embodiments, a lubricious coating can be applied to the proximal exterior surface 218 and/or the distal exterior surface 220. The lubricious coating can include parylene, mineral oil, silicone lubricant, and/or other lubricant or material. The lubricious coating can reduce friction between the proximal exterior surface 218 and a suture within the proximal suture receiving area 234. The reduction in friction can decrease the likelihood of the suture initiating a tear along the proximal exterior surface 218. In some embodiments, a lubricious coating can be provided along the proximal exterior surface 218 and/or the distal exterior surface 220, while the lubricious coating is not provided along the proximal end portion 222, the middle portion 228, the distal end portion 224, or the inner surface 230 of the lumen 226. The lack of lubricious coating along the inner surface 230 can ensure that the suture sleeve 208 can grip the lead 106. The lack of lubricious coating along the proximal end portion 222, the middle portion 228, and the distal end portion 224 can ensure that the clinician can handle the suture sleeve 208 during implantation of the lead 106. However, in some embodiments the lubricious coating can be provided along the entire exterior surface of the suture sleeve 208.

In some embodiments, the suture sleeve 208 can be doped with a dopant. For example, barium sulphate ($BaSO_4$) can be used as a dopant to make the material of the suture sleeve 208 radiopaque. Titanium dioxide ($TiO_2$) can also be used as a dopant or otherwise suspended or mixed within the material forming at least a portion of the suture sleeve 208 to color the suture sleeve 208. However, such dopants or additives can weaken the material in some configurations. In some embodiments, the surfaces of the proximal end portion 222, the middle portion 228, the distal end portion 224, and/or the inner surface 230 of the lumen 226 can be doped and/or can contain an additive while the proximal suture receiving area 234 and the distal suture receiving area 236 can be dopant and/or additive free to preserve the tear resistance of the proximal and distal exterior surfaces 218 and 220.

Figure 3:
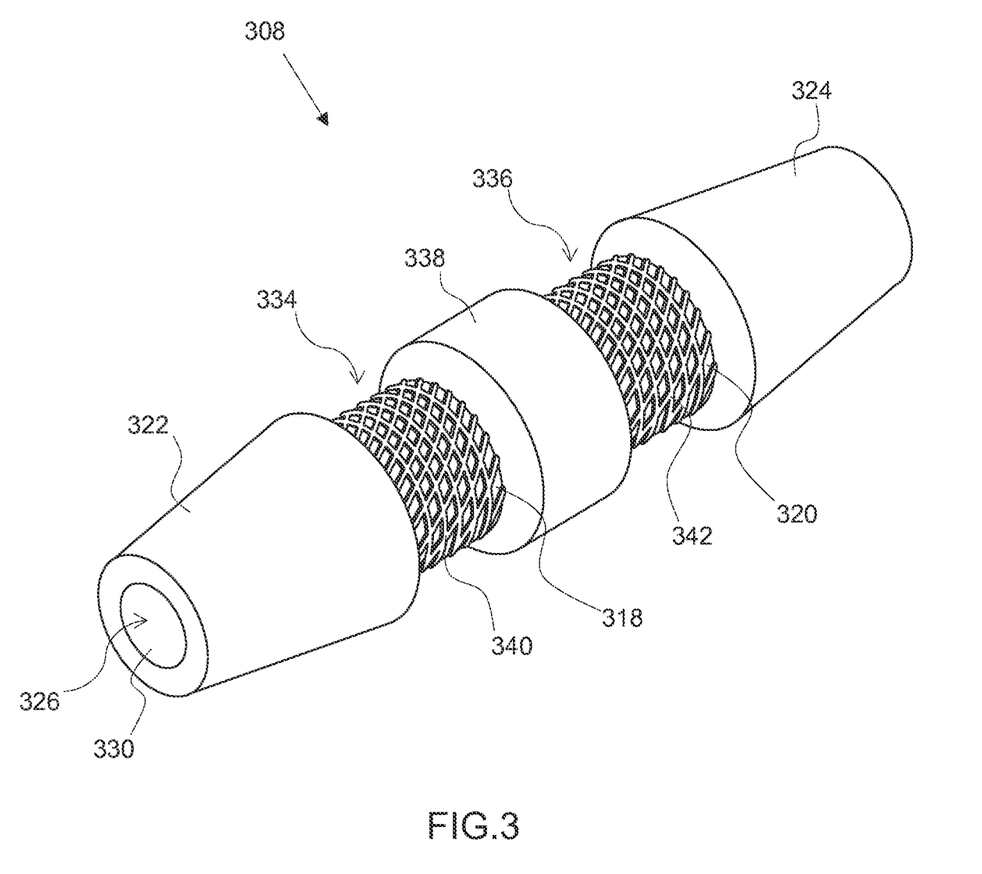
FIG. 3 is a perspective view of a suture sleeve having a textured portion on an exterior surface of the suture sleeve.

FIG. 3 is a perspective view of a suture sleeve 308. The suture sleeve 308 of FIG. 3 can correspond with the suture sleeves 108 and 208 of FIGS. 1A-2B. The suture sleeve 308 can include a proximal end portion 322, a middle portion 338, a proximal suture receiving area 334 between the proximal end portion 322 and the middle portion 338, a distal end portion 324, a distal suture receiving area 336 between the middle portion 338 and the distal end portion 324, and a lumen 326 that extends from the proximal end portion 322 to the distal end portion 324. Each of the proximal suture receiving area 334 and the distal suture receiving area 336 can be defined as a respective channel within the suture sleeve 308 that can contain sutures, the channels preventing the sutures from slipping off the suture sleeve 308.

Tear resistant features can be provided along each of the proximal exterior surface 318 and the distal exterior surface 320. In various embodiments, the tear resistant feature can comprise texturing on the proximal exterior surface 318 and the distal exterior surface 320. The texturing of the proximal exterior surface 318 and the distal exterior surface 320 can insulate the exterior surface of the suture sleeve 308 from torque stress from sutures wrapped around the proximal suture receiving area 334 and the distal suture receiving area 336. In this way, the texturing can resist initiation of a tear in the exterior surface of the suture sleeve 308.

In some embodiments, the texturing can comprise a raised pattern along the proximal exterior surface 318 and the distal exterior surface 320. For example, a plurality of raised features can be provided, such as the raised lines 340 and 342 in a crossing pattern along the proximal exterior surface 318 and the distal exterior surface 320. The raised lines 340 and 342 can be orientated to cross the longitudinal axis and/or the circumference of the suture sleeve 308 such that a suture wrapped around a part of the circumference of the suture sleeve 308 crosses over the raised lines 340 and 342. The crossing pattern as shown can prevent a suture from lodging in between raised lines. However, the present disclosure is not limited to crossing line patterns and various other patterns can be provided as a tear resistant feature.

In some embodiments, texturing of a tear resistant feature comprises a sunken pattern along one or both of the proximal exterior surface 318 and the distal exterior surface 320. Each sunken line can be in the form of a groove. For example, a pattern of grooves can be provided. In some embodiments, the pattern of grooves can comprise a plurality of crossing grooves (e.g., in the same pattern as the raised lines of FIG. 3). In some embodiments, the pattern of grooves can comprise a plurality of parallel grooves extending around the circumference of the proximal exterior surface 318 and the distal exterior surface 320. In some embodiments, each groove is dimensioned such that a suture can partially fit within a groove, but the groove is not so deep that the suture entirely fits within the groove. In some embodiments, the grooves can be triangular, V-shaped, rhomboidal, and/or rounded.

In some embodiments, the texturing comprises a pattern of dimples along one or both of the proximal exterior surface 318 and the distal exterior surface 320. Conversely, in some embodiments, the texturing can comprise a pattern of raised bumps (e.g., rounded bumps) along one or both of the proximal exterior surface 318 and the distal exterior surface 320. Additionally, in some embodiments, the texturing comprises etching along one or both of the proximal exterior surface 318 and the distal exterior surface 320. Various shapes can be etched in a pattern to provide a tear resistant feature. In some cases, material can be deposited over the proximal exterior surface 318 and/or the distal exterior surface 320 to provide a tear resistance feature. For example, a mesh of polymeric fibers or metallic fibers can be deposited to texture the proximal exterior surface 318 and/or the distal exterior surface 320. Various patterns of material can be deposited along the proximal exterior surface 318 and/or the distal exterior surface 320 by lithography to texture these surfaces as a tear resistant feature.

The texturing of the proximal exterior surface 318 can extend around the entire circumference of the proximal suture receiving area 334 (e.g., around the entire channel). Likewise, the texturing of the distal exterior surface 320 can extend around the entire circumference of the distal suture receiving area 336 (e.g., around the entire channel). In some embodiments, the texturing of the proximal exterior surface 318 extends longitudinally along the entire proximal suture receiving area 334 (e.g., between the proximal end portion 322 and the middle portion 338). Further, the texturing of the distal exterior surface 320 can extend longitudinally along the entire distal suture receiving area 336 (e.g., between the distal end portion 324 and the middle portion 338).

Several aspects of texturing can support tear resistance. For example, the texturing along the proximal suture receiving area 334 can reduce the amount of the proximal exterior surface 318 that is in contact with a suture due to empty spaces between the raised lines 340. Less surface contact can decrease the frictional resistance with the suture reducing the chance of a tear being initiated in the proximal exterior surface 318 from a suture. Other raised or sunken features, provided as an alternative to the raised lines 340, can likewise reduce the amount of surface contact between a suture and the proximal exterior surface 318 to reduce the likelihood of a tear being initiated along the proximal exterior surface 318.

Various methods can be used to manufacture the suture sleeve 308. For example, the tubular body of a suture sleeve 308 can be molded or extruded. In some cases, a single type of material can be extruded or molded to form the tubular body of the suture sleeve 308 and the material can be additionally processed along one or both of the proximal suture receiving area 334 and the distal suture receiving area 336 to add one or more tear resistant features, such as texturizing, a lubricious coating, and/or hardening of the material.

In some embodiments, the tear resistant feature is provided as part of the molding of the tubular body of the suture sleeve. For example, a suture sleeve can be molded with a textured pattern. In some other embodiments, the tear resistant feature is provided as a step separate from the molding of the tubular body. In such cases, a processing step can be performed on the tubular body to provide the tear resistant feature. For example, a lubricious coating can be applied to a section of a suture receiving area after the tubular body has been formed. In some cases, texturing can be formed on a section of a suture receiving area after the tubular body has been formed. In some cases, hardening of material of the tubular body can be formed on a section of a suture receiving area after the tubular body has been formed. In various embodiments, the processing step is only performed along a section of a suture receiving area (e.g., within a channel). In various embodiments, the processing step is not performed along a proximal end portion, a distal end portion, a middle portion, and/or along an interior surface of the lumen of the tubular body. In some embodiments, the processing step is performed along the entire exterior of a suture sleeve.

While the embodiments presented herein generally show two suture receiving areas (e.g., the proximal and distal 136 and 134 suture receiving areas) defined by respective channels, various embodiments may not have any channels. For example, a suture receiving area, and the tear resistant feature provided therealong, can extend along the entire exterior circumferential surface of a suture sleeve. Some embodiments may not include a channel but may have multiple suture receiving areas and associated tear resistant features provided therealong on the exterior surface of a suture sleeve, the suture receiving areas separated from each other along the suture sleeve. Some embodiments may only have a single channel defining a single suture receiving area, where a tear resistant feature is provided along the single suture receiving area. However, various embodiments can have a plurality of channels, each channel defining a respective suture receiving area, where a tear resistant feature is provided along each suture receiving area. For example, some embodiments can have three channels, each channel defining a respective suture receiving area, where a tear resistant feature is provided along each suture receiving area. As such, each of the suture sleeves of FIGS. 1-3 can be modified to have one, three, or some other number of channels defining respective suture receiving areas.

The suture sleeves described above and otherwise wherein can be modified in view of any other embodiment presented herein, as the present application provides examples of various features that are selectively useable together and are not presented in a restrictive sense. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

We claim:

1. A suture sleeve for securing an implantable lead with at least one suture, the suture sleeve comprising:
    a tubular body having a proximal end portion and a distal end portion;
    a lumen within the tubular body extending from the proximal end portion to the distal end portion, the lumen sized to receive the implantable lead;
    at least one suture receiving area along the tubular body, the at least one suture receiving area respectively defining at least one exterior surface respectively within at least one channel that extends around a circumference of the tubular body;
    a tear resistant feature extending only along the at least one exterior surface within the at least one channel, the tear resistant feature comprising a textured pattern configured to resist initiation of a tear in the at least one exterior surface from the at least one suture; and
    an inner surface within the lumen, the inner surface configured to frictionally engage the implantable lead.

2. The suture sleeve of claim 1, wherein the textured pattern is raised from the at least one exterior surface and is configured to insulate the at least one exterior surface from torque stress from the at least one suture.

3. The suture sleeve of claim 1, wherein the textured pattern is configured to reduce the surface area of the at least one exterior surface of the at least one suture receiving area in contact with the at least one suture when the at least one suture is placed along the at least one suture receiving area.

4. The suture sleeve of claim 1, wherein the textured pattern comprises a pattern of crossing raised lines.

5. The suture sleeve of claim 1, wherein the textured pattern comprises a plurality of dimples.

6. The suture sleeve of claim 1, wherein the textured pattern comprises a pattern of grooves.

7. The suture sleeve of claim 1, wherein the tear resistant feature reduces friction between the at least one exterior surface and the at least one suture when the at least one suture is placed within the at least one channel of the suture receiving area.

8. The suture sleeve of claim 1, wherein:
    the tear resistant feature further comprises a hardened material defining the at least one exterior surface of the suture receiving area; and
    the at least one exterior surface of the suture receiving area is harder relative to the inner surface within the lumen.

9. The suture sleeve of claim 1, wherein the at least one exterior surface of the suture receiving area is formed from a first material and the inner surface of the lumen is formed from a second material, the first material having a higher durometer than the second material.

10. The suture sleeve of claim 1, wherein the at least one suture sleeve is made from a single type of material and processed along the suture receiving area to form the tear resistant feature.

11. The suture sleeve of claim 1, wherein the tear resistant feature further comprises a lubricious coating.

12. The suture sleeve of claim 1, wherein:
the at least one suture receiving area is between the proximal end portion and the distal end portion; and
the at least one channel of the suture receiving area is dimensioned such that a section of each of the at least one suture does not extend above the proximal end portion and the distal end portion when the section of the suture is within the at least one channel and contacts the at least one exterior surface of the at least one suture receiving area.

13. The suture sleeve of claim 1, wherein the at least one channel comprises a plurality of channels, the at least one exterior surface comprises a plurality of exterior surfaces respectively within the plurality of channels, and the textured pattern extends only along the plurality of exterior surfaces within the plurality of channels.

14. The suture sleeve of claim 13, wherein the plurality of channels comprise two channels that are separated by a middle portion of the tubular body, the middle portion having an outer diameter that is greater than respective outer diameters of the plurality of exterior surfaces of the two channels.

15. A suture sleeve for securing an implantable lead with at least one suture, the suture sleeve comprising:
a tubular body having a proximal end, a distal end, and at least one channel that extends around a circumference of the tubular body, the at least one channel configured to receive the at least one suture;
a lumen within the tubular body extending from the proximal end to the distal end, the lumen sized to receive the implantable lead;
at least one exterior surface within the at least one channel;
a lubricious coating disposed only on the at least one exterior surface within the at least one channel, the lubricious coating configured to reduce friction between the at least one exterior surface and the at least one suture;
an inner surface within the lumen, the inner surface configured to frictionally engage the implantable lead.

16. The suture sleeve of claim 15, wherein the at least one exterior surface is formed from a first material, the inner surface of the lumen is formed from a second material, the first material has a higher durometer than the second material, and the first material is extruded over the second material to form the tubular body.

17. The suture sleeve of claim 16, wherein the second material is silicone and the first material comprises one or both of a polymer material and a metal material.

18. A method of making a suture sleeve for use with at least one suture for securing an implantable lead, the method comprising:
forming a tubular body having a proximal end portion, a distal end portion, a lumen sized to receive the implantable lead, an inner surface within the lumen, and at least one channel around the circumference of the tubular body, the at least one channel comprising at least one exterior surface, the at least one channel sized to accommodate the at least one suture within the at least one channel, respectively; and
forming a textured pattern on the at least one exterior surface in the at least one channel, the textured pattern providing a tear resistance property of the at least one exterior surface, wherein the textured pattern is only formed on the at least one exterior surface within the at least one channel.

19. The method of claim 18, further comprising processing the at least one exterior surface along the at least one channel to harden a material that forms the at least one exterior surface.

20. The method of claim 18, wherein the textured pattern is formed to be raised from the at least one exterior surface along the at least one channel.

* * * * *